United States Patent [19]

Snyder

[11] Patent Number: 4,820,047

[45] Date of Patent: Apr. 11, 1989

[54] LASER HETERODYNE APPARATUS FOR MEASURING OPTICAL POWER

[76] Inventor: James J. Snyder, 707 Broadmoor Dr., San Jose, Calif. 95129

[21] Appl. No.: 136,919

[22] Filed: Dec. 22, 1987

[51] Int. Cl.$^4$ .............................................. G01B 9/02
[52] U.S. Cl. ................................................ 356/349
[58] Field of Search ......................... 356/5, 28.5, 349

[56] References Cited

U.S. PATENT DOCUMENTS 3,857,636 12/1974 Angelbeck ........................ 356/349

Primary Examiner—Vincent P. McGraw
Assistant Examiner—S. A. Turner
Attorney, Agent, or Firm—Joseph H. Smith

[57] ABSTRACT

A detection system is provided which has a very wide linear dynamic range (for a typical laser, fifteen orders of magnitude), as well as a high sensitivity (shot noise limited), high angular resolution (diffraction limited), and which is also polarization resolving. The apparatus is used for measuring optical power, and includes a system for producing two optical beams such that at some point and thereafter along an optical path of the beams, a frequency difference exists between the two beams, with one of the two beams having a known or constant optical power, and the other of the two beams being the beam whose power is to be measured. Also included is a combining element for coherently combining the two optical beams. An optical detection system receives the combined two optical beams, and in response thereto provides an electrical signal that is modulated at the difference frequency of the optical fields of the two optical beams, the electrical signal being functionally related to the heterodyne product of the two fields. An electrical power detector is then used for measuring the electrical power of the electrical signal. Several embodiments are described which use the basic power measuring system to characterize optical filters, to measure optical density of photographic plates, to measure BRDF and BTDF, and to provide a well calibrated laser radiation source which is particularly well suited for very low power applications.

13 Claims, 11 Drawing Sheets

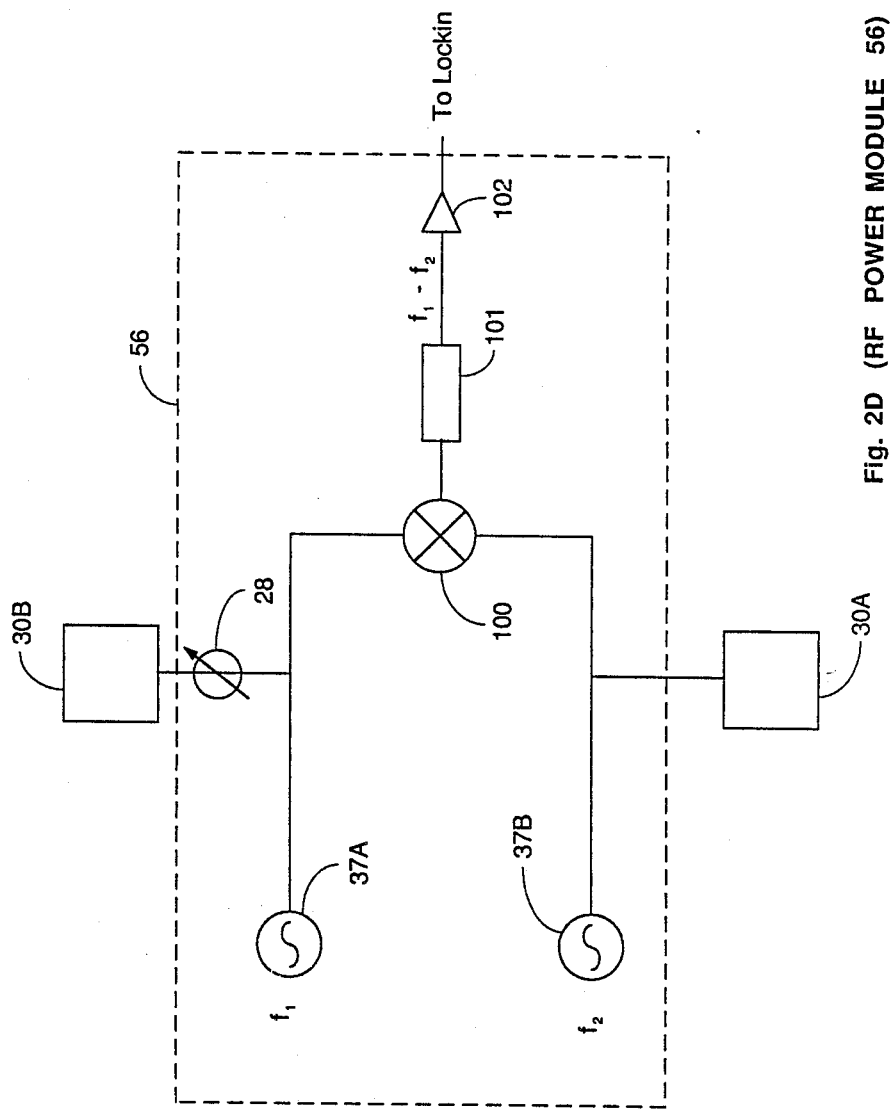
Fig. 2D (RF POWER MODULE 56)

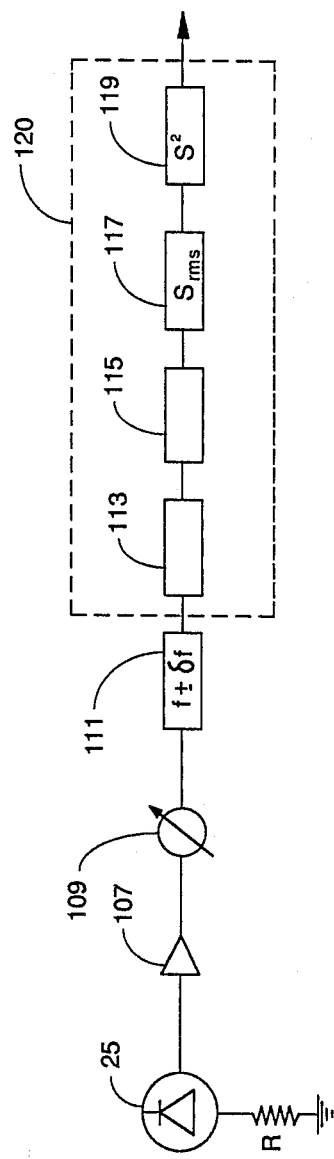
Fig. 2E (DETECTOR 32)

LASER HETERODYNE APPARATUS FOR MEASURING OPTICAL POWER

BACKGROUND OF THE INVENTION

This invention pertains to the use of laser heterodyne detection in interferometry, particularly as it relates to methods and apparatus for very accurately characterizing optical filters, measuring optical density of photographic plates or films, providing a well calibrated source of very low power laser radiation, and making measurements of the bidirectional reflectance distribution function (BRDF) and bidirectional transmittance distribution function (BTDF) of surfaces.

At the present time, instruments used for these purposes utilize direct, or incoherent detection, and incorporate detectors such as photomultipliers, photoconductors, or photodiodes. Problems inherent in such systems are of several kinds. In particular, they have a restricted dynamic range, e.g. the linear dynamic range of a photomultiplier is typically no more than five to six orders of magnitude. Photodiodes, the best of these detectors in terms of dynamic range, are linear over a range of about seven or eight orders of magnitude, but are limited in terms of sensitivity. Also, measurements are often desired over a much wider dynamic range than that which is available even with the photodiode. In addition, the photomultiplier, which has the greatest sensitivity, has the smaller dynamic range. Hence, accurate measurements can only be made over a limited dynamic range, and in practice the photomultiplier is used primarily as a null detector. (See W. Budde, _Optical Radiation Measurements_. Vol. 4, Academic Press, 1983, for a general reference regarding optical detectors.)

Another problem also often encountered using such incoherent detection schemes concerns angular resolution. In practice, it is difficult to achieve high angular resolution without encountering unacceptable losses in sensitivity. Also, such systems are not inherently polarization sensitive, and hence require additional elements to characterize the polarization of the detected beam.

What is needed is a detection system which has a significantly improved linear dynamic range and is also shot noise limited in sensitivity.

SUMMARY OF THE INVENTION

In accordance with preferred embodiments of the invention, a detection system is provided which has a very wide linear dynamic range (for a typical laser, fifteen orders of magnitude), as well as a high sensitivity (shot noise limited), high angular resolution (diffraction limited), and which is also polarization resolving.

In the general case, the apparatus is used for measuring optical power, and includes a system for producing two optical beams such that at some point and thereafter along an optical path of the beams, a well defined frequency difference exists between the two beams, with one of the two beams having a known or constant optical power, that beam hereinafter called the reference beam, and the other of the two beams being the beam whose power is to be measured, that measured beam hereinafter called the test beam. Also included is a combining element for coherently combining the two optical beams. An optical detection system receives the combined two optical beams, and in response thereto provides an electrical signal that is modulated at the difference frequency of the optical fields of the two optical beams, the electrical signal being functionally related to the heterodyne product of the two fields. An electrical power detector is then used for measuring the electrical power of the electrical signal.

In one preferred embodiment, the basic optical power measuring system of the invention is used to measure the optical density of filters. In that embodiment, the system includes an insertion element for inserting and removing a filter from the path of the test beam. Then the filter density can be determined from the resulting change in the heterodyne product of the two optical powers with the filter in the path of the test beam relative to not having the filter in the test path by measuring the change in electrical power.

In another preferred embodiment, the system also includes a focussing system for focussing the test beam onto a photographic plate, so that the test beam is attenuated in a manner related to the local optical density of the plate. The transmitted beam is then recollimated and output to the combining element. Also included is a translation system for moving the photographic plate so that the test beam is focussed onto different portions of the photographic plate at different times, in order to provide an optical density map of the photographic plate.

In yet another preferred embodiment of the invention, the system is used to measure BRDF or BTDF. In that embodiment, the apparatus includes a goniometer for holding a surface in the path of the test beam in a desired orientation relative to the incidence direction of the test beam, and a moving element for moving the optical detector so as to receive light from one or a plurality of known second directions, that light having been scattered or reflected or transmitted from the surface as a result of the incidence of the test beam on the surface. Also included is a calculation element for calculating the ratio of the radiance in the one or plurality of known second directions to the incident irradiance of the test beam. In the preferred mode, the apparatus also includes a platform on which the optical detector is mounted, the platform being rotatable about the surface. In addition, the apparatus includes an optical fiber, in order to transmit the reference beam to the optical detector on the rotatable platform. A particular benefit of the detection scheme in this scheme is that scattering measurements can be made remotely from the test surface, e.g. in hazardous environments.

In another preferred embodiment, the optical power measuring system is used to provide a very well calibrated low power optical source. In that embodiment, the apparatus includes an attenuator for varying the optical power in the test beam, and a beam splitter in the test arm located upstream from the combining element, the beam splitter being used to provide an output beam that is a portion of the test beam. Also included is an optical power detector for measuring the optical power of the output beam, and an insertion element for inserting and removing the optical power detector from the path of the output beam, so that an attenuated test beam can be provided when the insertion element is removed from the path of the output beam. The optical power detector serves to calibrate the RF heterodyne electrical power detection system when the optical power in the test beam is at a value that can be readily measured. Then the RF heterodyne electrical power detection system can be used to monitor the optical power in the test beam as the attenuator is used to reduce the power in the output beam.

BRIEF DESCRIPTION OF THE DRAWINGS

FIG. 2D shows the details of an RF power supply for the embodiment of FIG. 2C.

FIG. 2E shows a simplified RF power detection system in accordance with a preferred embodiment of the invention.

DETAILED DESCRIPTION OF THE PREFERRED EMBODIMENTS

Figure 1:
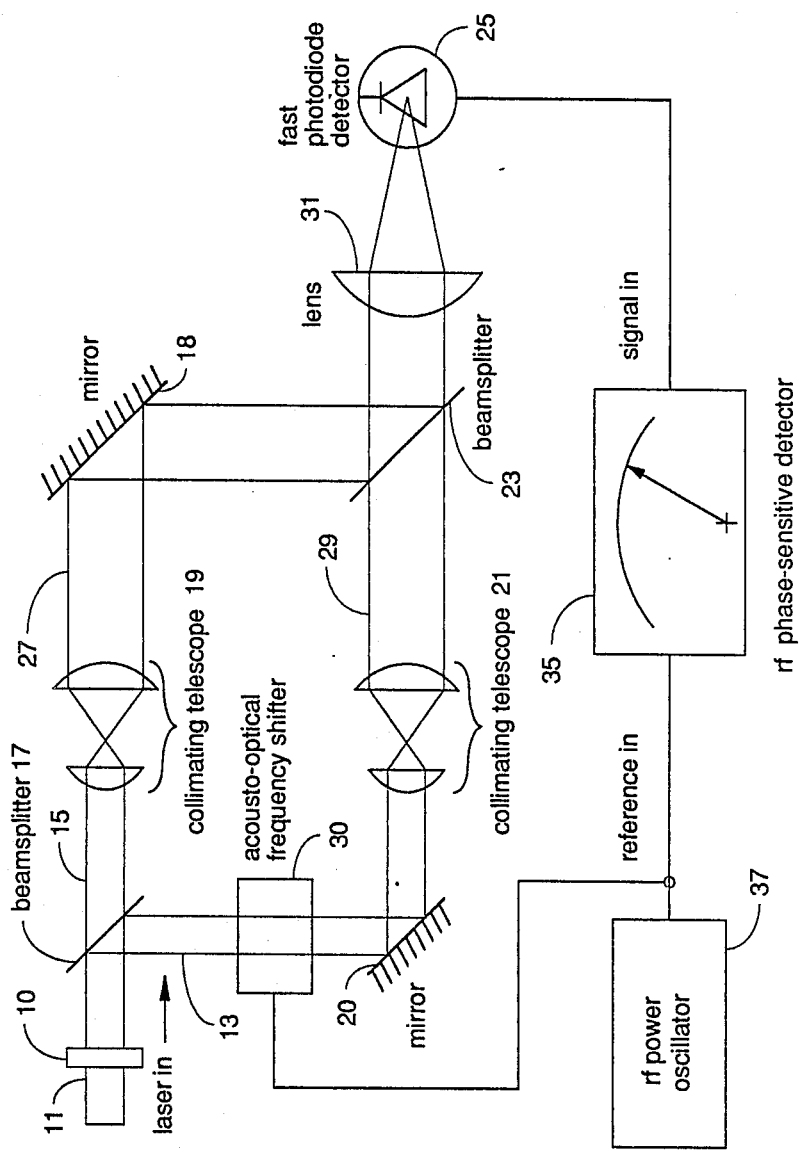
FIG. 1 shows a prior art heterodyne interferometer.

The concept of the invention is best understood by first considering the simple prior art Mach-Zehnder heterodyne laser interferometer as shown in FIG. 1. An input laser beam 11 is divided into two beams 13 and 15 by a first beamsplitter 17. Each beam may be expanded or reduced as desired by a collimating telescope in the corresponding arm of the interferometer, such as telescopes 19 and 21. After reflection by mirrors 18 and 20, a second beamsplitter 23 recombines the two beams for heterodyne detection at the photodiode 25. One of the interferometer arms, arm 27, is designated the reference arm. The optical power in the reference arm, as measured at the photodiode, will be denoted by $P_0$. The other arm 29 is designated the test arm, and its optical power will be denoted by $P_1$. The optical frequency of the light in the test arm is shifted by some radio frequency (RF) amount f (e.g., by an acousto-optic modulator 30 that is driven by an RF power oscillator 37) relative to the optical frequency of the light in the reference arm. When the beams from the two arms of the interferometer are combined and focussed onto the photodiode by lens 31, a modulated heterodyne current is produced by the photodiode at the beat frequency f.

For highest sensitivity, the RF beat frequency signal from the photodiode is detected coherently by mixing with an RF reference signal at the same frequency. This may be accomplished with the use of a commercially available phase sensitive detector 35 referenced to the same signal source 37 that drives the acousto-optic modulator.

For the usual case where the combined power of the reference and test laser beams is small enough that the photodiode operates in the linear regime, the modulated signal current from the photodiode 25 may be written as $$i(t) = k(P_0 P_1)^{\frac{1}{2}} \cos(2\pi f t + \phi),$$

where $\phi$ is the optical phase difference between the two beams and $k = en/hv$. Here e is the electric charge, n is the detector quantum efficiency, h is Planck's constant and v is the optical frequency of the laser radiation. The amplitude of the RF current at frequency f is proportional to the square root of the product of the optical field powers, and is therefore proportional to the product of the field amplitudes. If the reference beam power is known, and both beams are accurately collimated and colinear after combining by beamsplitter 23, then the complex field amplitude of the test beam is found from the phase and amplitude of the photodiode signal at frequency f. It should be noted that in most prior applications of heterodyne interferometers such as that shown in FIG. 1, only a measurement of the optical phase $\phi$ is desired because it is related to differences in the optical path lengths of the two beams, 27 and 29, within the interferometer.

In order to measure the phase $\phi$ and amplitude $k(P_0 P_1)^{\frac{1}{2}}$, the RF beat frequency signal from the photodiode is detected coherently by mixing with an RF reference signal at the same frequency. This may be accomplished with the use of a commercially available phase sensitive detector 35 referenced to the same signal source 37 that drives the acousto-optic modulator.

For highest sensitivity, the beat frequency f is generally chosen to be no less than one or two MHz in order to be above the laser technical, or excess noise bandwidth, which for typical lasers is 100 kHz or higher. The heterodyne detection sensitivity for frequencies greater than a few milliwatts, will be limited only by shot noise fluctuations in the reference beam. The minimum reference beam power necessary for shot-noise limited sensitivity depends on the internal noise (i.e., sensitivity) of the phase sensitive detector 35, or other means used to measure the beat frequency signal.

The laser heterodyne detector is sometimes characterized as a "single mode optical receiver". That is because the photodiode beat signal is maximized if the mode of the test beam exactly matches the mode of the reference beam, but approaches zero if the mode of the test beam differs from the reference beam. If both the reference and test beams are superimposed and collimated, then "mode matched" means that the beams are parallel. The required degree of parallelism, i.e., the angular resolution (full width, half maximum) of the laser heterodyne detector, is given by $\delta\theta \approx \lambda/2D$, where $\lambda$ is the laser wavelength and D is the beam diameter.

What is generally not appreciated is the extremely wide dynamic range that is characteristic of the laser heterodyne receiver. The optical power measurement sensitivity for the laser heterodyne detector may be estimated by assuming that the measurement noise is dominated by the shot noise of the reference laser beam. With sufficient cw laser power (a few milliwatts), this will often be the case if the heterodyne beat frequency is above the technical noise bandwidth of the laser (approximately 1 MHz). Then the signal-to-noise power ratio of the detected RF signal is $$(S/N)_p = <i_s^2>/<i_n^2>$$

where the average mean-squared signal current at frequency f is $$<i_s^2> = 2e^2 n^2 P_1 P_0/(hv)^2$$

and the average mean-squared shot noise current due to the reference laser beam is $$\langle i_n^2 \rangle = 2P_0 e^2 n \Delta v / hv$$

for a detection bandwidth $\Delta v$. If we define the sensitivity to be the optical power $(P_1)_{min}$ such that the signal-to-noise ratio is one, then $$(P_1)_{min} = hv \, \Delta v / n.$$

This result implies a sensitivity of one detected test photon per sample time of the instrument; i.e., the sensitivity is limited by the statistical fluctuations or shot noise of the test beam. As an example, if we assume $\Delta v = 1$ Hz and $n \approx 1$, then for a laser at 633 nm the sensitivity is $$(P_1)_{min} = 3 \cdot 10^{19} \, W.$$

The upper limit for the optical power in the test arm is determined by the maximum total power incident on the photodiode for which it still responds linearly. If we assume $P_0 \approx (P_1)_{max} \approx 1$ mW, then the dynamic range of the basic laser heterodyne detector is approximately $10^{15}$ in optical power.

Optical Power Measurements

Figure 2A:
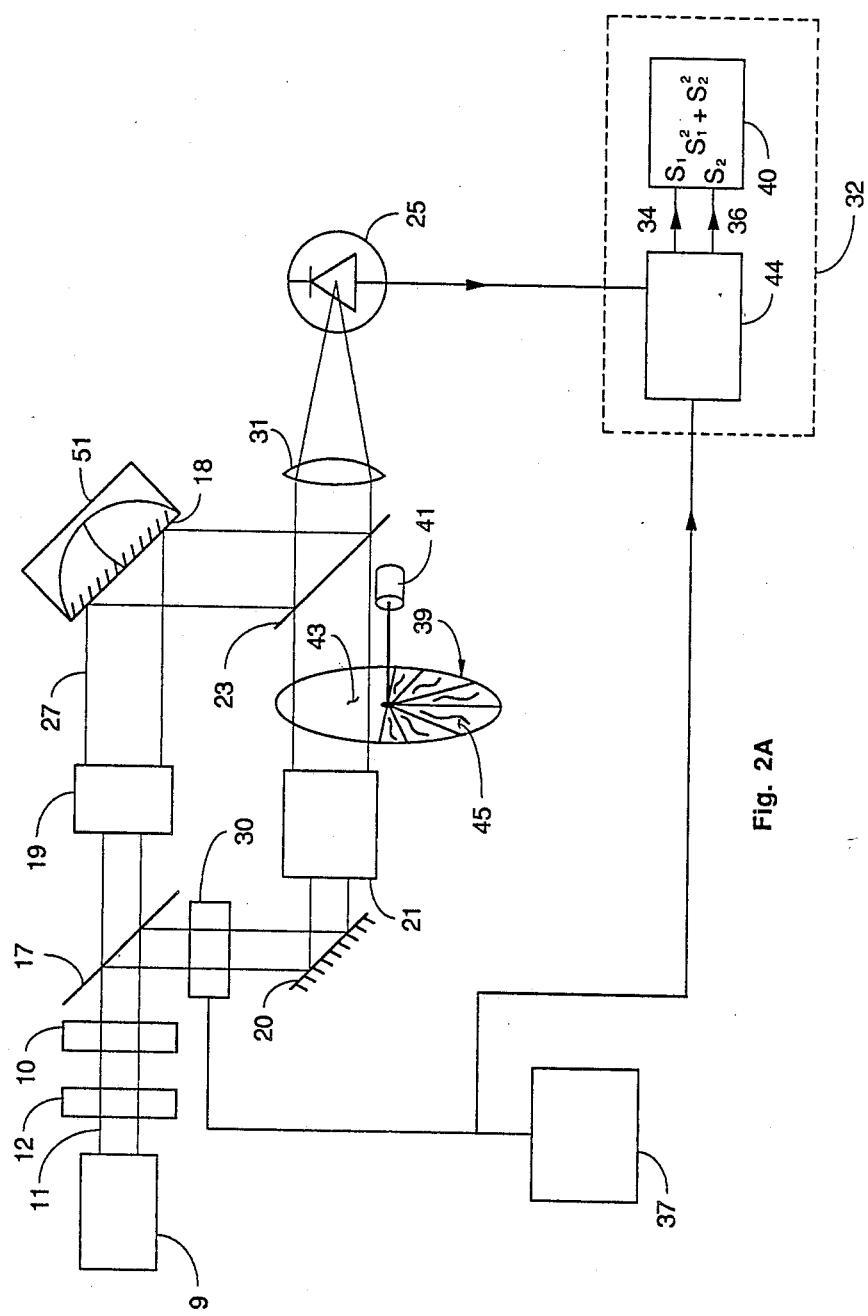
FIG. 2A shows an apparatus according to the invention for measuring the transmission coefficient of optical filters.
Figure 2B:
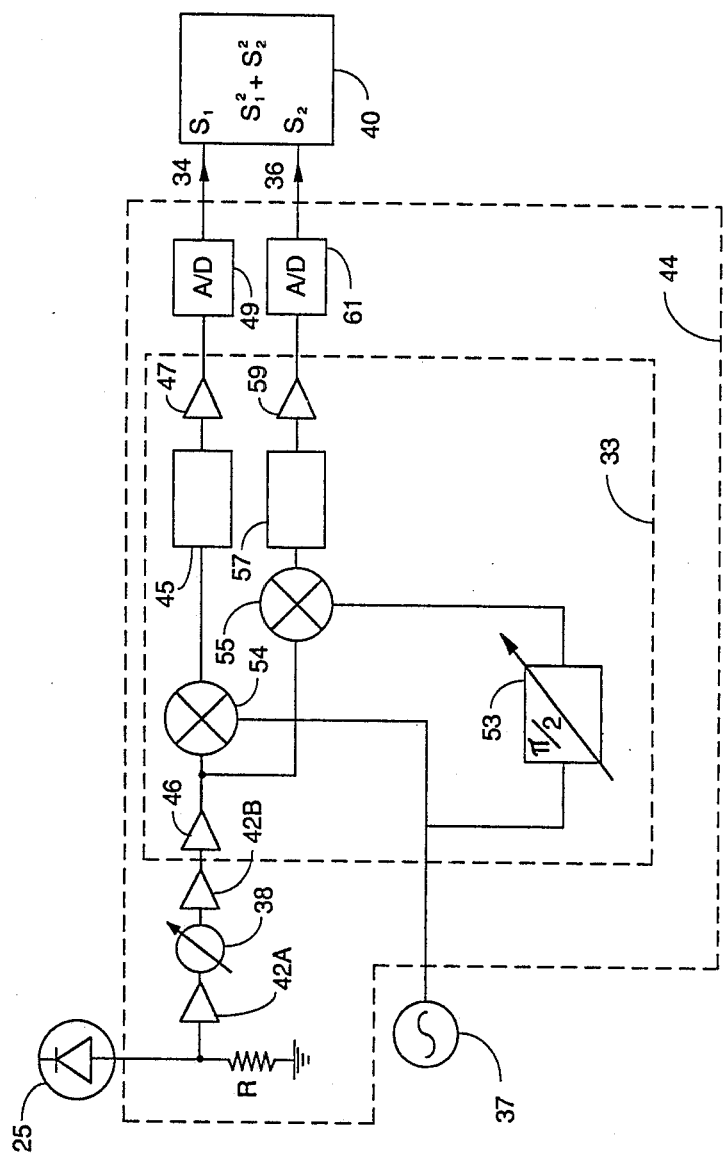
FIG. 2B shows the details of a lock-in detector used in the apparatus of FIG. 2A.

By modifying the basic heterodyne detection system of FIG. 1 according to the invention as illustrated in FIG. 2A and measuring RF power, instead of phase as has been done in the prior art, it is possible to very accurately measure changes in laser optical power caused by transmission of the test beam through media such as neutral density filters, absorption filters, scattering or reflecting media, dielectric filters, sea water, optical filters, and the like. For the purposes of this discussion, all such media will be referred to hereinafter simply as filters. As illustrated in FIG. 2A, the system according to the invention includes several additional elements not shown in FIG. 1. In particular, instead of measuring phase, as such, the output of the photodetector 25 and the output of reference oscillator 37 form the input to a narrow band, tracking, RF power meter 32. The power meter 32, in the preferred mode, includes a lock-in detector 44 and a computer 40. In response to the photodetector output signals, the lock-in detector 44 provides a digitized in-phase signal $S_1$ on signal line 34 and a digitized quadrature phase signal S, on signal line 36. These signals $S_1$ and $S_2$ are squared and summed by the computer 40 (or equivalently by analog electronic circuitry) to calculate the RF power from the photodetector at the frequency f. FIG. 2B shows a more detailed schematic of the RF power detector 32, including specifically the details of the lock-in detector 44. Detector 44 is essentially a lock-in amplifier 33 followed by two analog-to-digital (A/D) converters 49 and 61. The output signal from the photodetector is typically amplified by analog preamplifiers 42A and 42B. Due to the very wide range of signal levels out of the photodetector 25, the output signal from preamplifier 42A is attenuated by a precision variable RF attenuator 38 to provide a signal level within the working regime of the preamplifier 42B. The other input to the lock-in amplifier is of course the signal from the RF reference oscillator 37.

By knowing the shot noise electrical power out of the detector 25, one can then readily calculate the required gain for the combination of amplifiers 42A and 42B, in order to have a useable output signal, i.e. within the working regime of the lock-in amplifier 33. The shot noise out of the detector, using a 10 mW local oscillator power at 1.06 μm and a 1 Hz detection bandwidth, is about $-160$ dBm. For a commercially available lock-in amplifier, such as an EG&G PAR 5202 high frequency lock-in amplifier, a typical preamplification of 70 to 80 dB is used. Also, the dynamic range of the RF detection system is generally directly related to the dynamic range of the RF attenuator, since the typical dynamic range of the lock-in amplifier is much less than 15 decades. Because of the extremely wide dynamic range of the system, it is often desired to work in a computer controlled mode. In that instance, the attenuator 38 is a computer controlled step attenuator, so that the computer 40 can control the attenuation level by means of a software feedback loop, in order to maintain a useable output signal.

For those who are not familiar with lock-in amplifiers, a typical one is illustrated in FIG. 2B and includes an amplifier 46 for multiplying the output signal from the amplifier 42B. A phase shifter 53 is used to shift the RF reference signal of the power oscillator 37 by ninety degrees. Multipliers 54 and 55 are used to multiply the signal from amplifier 46 by the reference signal from oscillator 37 and by the signal from phase shifter 53, respectively. Each of the resulting signals is then passed through a low pass filter, such as filters 45 and 57, to provide the in-phase and quadrature-phase RF signals, and the resulting signals are then amplified by amplifiers 47 and 59. As described earlier, the A to D converters 49 and 61 following the lock-in amplifier 33 then digitize these RF signals for input to the computer 40.

With reference to FIG. 2A, also shown is a transmissive medium, illustrated schematically by a filter wheel 39, having an open window section 43 for transmitting the test beam without attenuation and a filter section 45 containing a medium through which the beam is to be transmitted. A motor 41 is used to rotate the filter wheel 39. Together the filter wheel and motor constitute a system for inserting and removing the filter section 45 from the test beam. Those skilled in the art will appreciate that there are many equivalent approaches that can be used for inserting and removing test filters.

Also in the preferred mode, it is typically best to mount the mirror 18 in an adjustable mount 51 that provides for rotational adjustment about two orthogonal axes in the plane of the mirror. This adjustment of the orientation of the mirror 18 may be necessary to compensate for any wedge effects that might be introduced by the filter when it is inserted. In addition, it is preferred to locate the mirror 18 and the filter wheel 39 equidistant from the beam-splitter 23 in order to prevent possible signal loss due to beam walkoff. Also, it is preferred to use an optical isolator 12 in the input path 11 from the laser in order to prevent any feedback into the laser which might cause spurious signals at the photodetector. Similarly, it is preferred to use an intensity stabilizer 10 after the isolator in order to appropriately condition the power being input into the system.

With the apparatus of FIGS. 2A and 2B, the relative power transmission can be measured with the filter in the test path, and with the filter out of the test path. If $i_1$ is the rms photodiode current without the filter in the test path, and $i_2$ is the rms photodiode current with the filter in the test path, then $$P_{1RF} = (i_1)^2 \cdot R = \alpha P_0 \cdot P_1, \text{ and}$$

$$P_{2RF} = (i_2)^2 \cdot R = \alpha P_0 \cdot P_2,$$

where R is the photodetector load resistance (e.g., 50Ω), where $P_0$ is the optical power in the reference beam 27, $P_1$ is the optical power in the test beam 29 with the filter out, $P_2$ is the optical power in the test beam 29 with the filter in the path, and α is a constant of proportionality.

$$\frac{P_{1RF}}{P_{2RF}} = \frac{P_2}{P_1} = T$$

where T is the filter transmittance, i.e., the ratio of the RF power out of the photodiode with the filter in the test path versus the RF power out of the photodiode with the filter out of the test path is the filter transmittance. Because detection system 32 is capable of measuring coherent RF power over a very wide dynamic range, a very wide dynamic range of optical power can be detected by this approach. This is a particularly important result since heretofore apparatus for measuring optical power over a very wide dynamic range has not been readily available. Hence, making accurate measurements of the transmittance of high density filters has been quite difficult or even impossible.

Figure 2C:
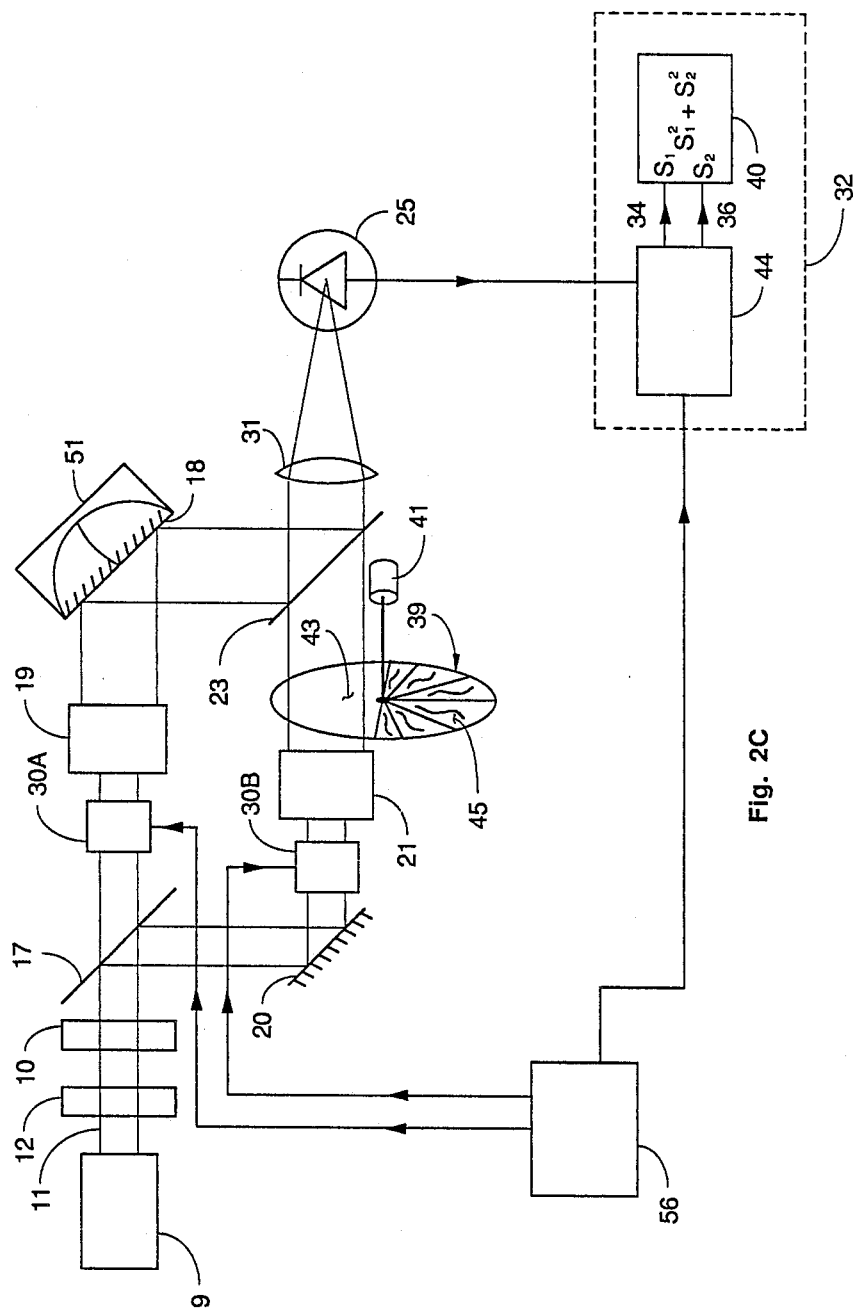
FIG. 2C shows an alternative embodiment of FIG. 2A which has very low noise characteristics.

A variation of the embodiment illustrated in FIG. 2A which has even better noise characteristics is shown in FIG. 2C. In this embodiment, two acousto-optic modulators 30A and 30B are used, one in each arm, to shift the beam frequency in each arm by RF frequencies $f_1$ and $f_2$, respectively. RF power for the modulators is provided by power module 56, which is illustrated in more detail in FIG. 2D. The power module includes two sources of RF power 37A and 37B, one at the frequency $f_1$ and the other at frequency $f_2$ for the frequency shifters. The power path to the test arm modulator 30B includes a variable attenuator 28 in order to control the output power of the system. A multiplier 100 multiplies the two signals from 37A and 37B, and a low pass filter 101 is used to pass only the signal having the frequency $f_1 - f_2$. That signal is then amplified by RF amplifier 102 to provide the reference signal needed by the RF power meter 32. With this embodiment, there is no high power RF signal at the frequency of detection, and hence electromagnetic interference in the output signal is significantly reduced.

In situations where wide detection bandwith or low sensitivity is desired, one may not need to use a heterodyne RF power detection scheme. In that case detector 32 can be much simpler. Such an example is illustrated in FIG. 2E. There, the output signal from the photodetector 25 is first amplified by amplifier 107 and then reduced to a useable amplitude level by an RF variable attenuator 109. The signal is then passed through a band pass filter 111 to isolate the beat signal. The beat signal is then detected by an RF power meter 120. As a simple example, the power meter 120 would include a rectifier 113 to provide a signal that is always positive. Then the signal is averaged by a low pass filter 115. The RMS amplitude is then measured by voltmeter 117, and is squared by element 119 to yield the average RF power.

Figure 3:
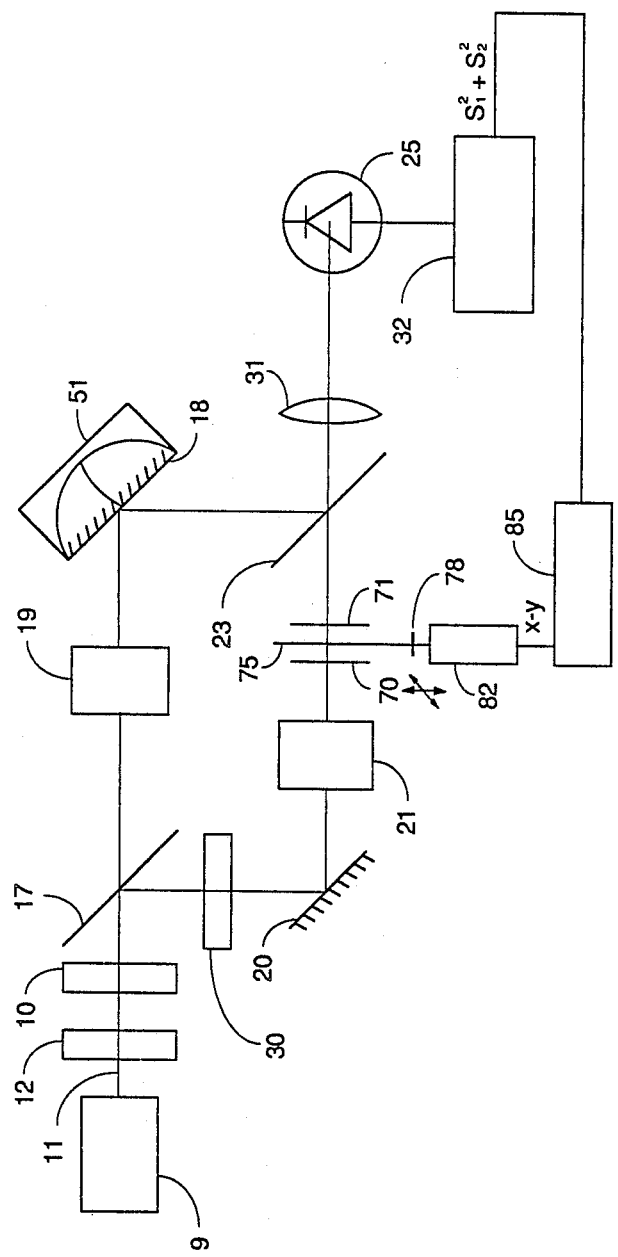
FIG. 3 shows an apparatus according to the invention for mapping the optical density of photographic film.

Shown in FIG. 3 is a second application of the concept of the invention which is adapted for high speed measurement of the optical density of photographic films. In this embodiment, a photographic plate or film negative 75 is mounted in the path of the interferometer by a movable mounting element 78, with the normal of the plate in the direction of the incident beam. A lens 70 is used to focus the incident beam at the plane of the plate, and a second lens 72 is used to collimate the beam again for incidence on beamsplitter 23. An automated X-Y translation system 82 in conjunction with the movable mounting element 78 is used to translate the plate back and forth in the path of the incident beam, so that the beam essentially traces out a raster scan of the plate. The control signals used in the translation system and the output signal corresponding to RF power measured by detector 32 form the input to a computer system 85 which correlates the X-Y position of the plate with the RF power measured at each position to arrive at a density map of the plate. In this embodiment, it appears that phase coherent detection is not required to achieve adequate information regarding optical density of photographic plates or films. Hence, a simpler RF power detection scheme could also be used, e.g. a bandpass filter followed by an RF power meter such as described with reference to FIG. 2E.

Figure 4A:
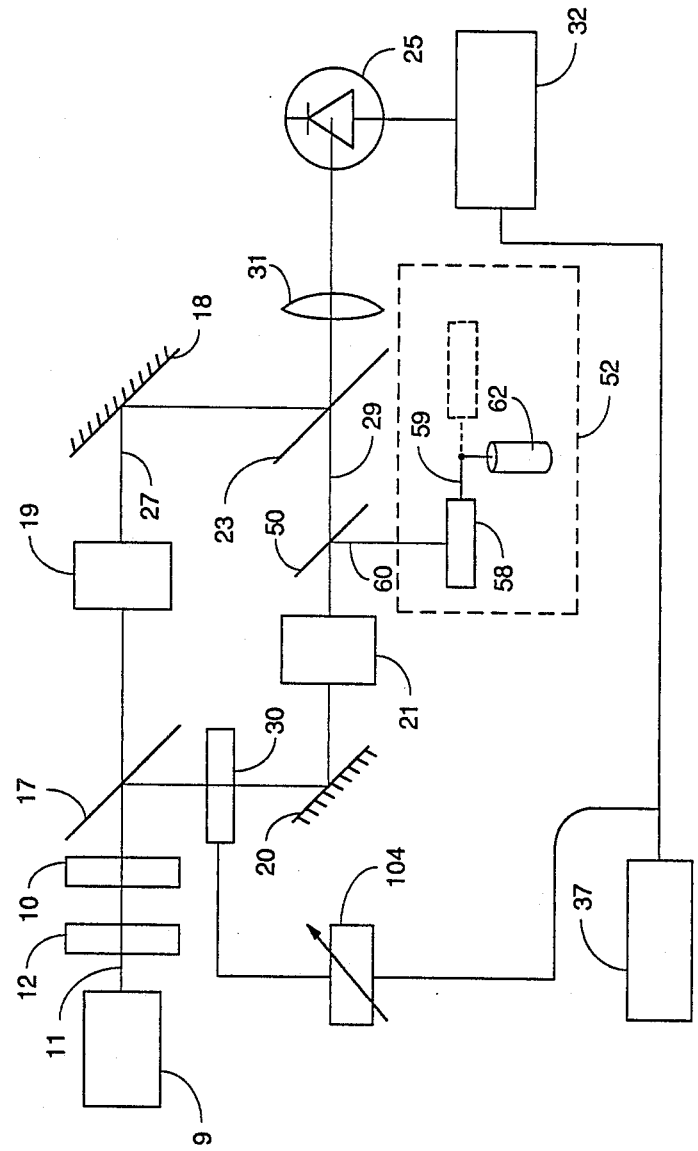
FIG. 4A shows an apparatus according to the invention for providing a source of very low power coherent light.

Shown in FIG. 4A, is another variation of the basic interferometer of the invention which makes use of the very wide dynamic range of the system to supply well calibrated, very low power laser light, e.g. such as might be desireable in testing the characteristics of optical detection systems. This exemplary embodiment includes the elements of the basic interferometer of FIG. 2A. An RF variable attenuator 104 is used to vary the power supplied by the RF oscillator 37 to the acousto-optic frequency shifter 30. In addition, a movable optical power detector system 52 is provided which is made up of a standard calibrated optical power monitor 58 attached to an arm 59 that is mounted on the shaft of a drive motor 62, so that the optical power detector can be moved into and out of the beam as desired.

To provide a well-calibrated power level for an output optical beam 60, with the system of FIG. 4A, the RF power to the acousto-optic modulator 30 is adjusted using RF attenuator 104 until the power delivered to the optical power monitor 58 is at a desired level, e.g. such as can be readily measured with a standard optical power monitor, typically about 1.0 mW. The RF power out of the photodiode 25 measured by the RF power detector 32 is recorded simultaneously with the optical power of output beam 60 as measured by the optical power monitor 58, these two measurements constituting a calibration of the output of the RF power detector 32. For example, suppose the optical power of 1.0 mW yields an RF power of 10 mW. The detector system is then calibrated at a ratio of 10 to 1, measured RF power to measured optical power. After calibration, the arm 59 supporting the optical power monitor 58 is then rotated by motor 62 to remove the optical power monitor 58 from the path of the output beam 60. Then the power to RF attenuator 104 is adjusted to achieve whatever optical power is desired in the beam 60, using RF power meter 32 to monitor the adjustment, since the optical power in beam 60 will be exactly one-tenth of the RF power measured by RF power meter 32.

Figure 4B:
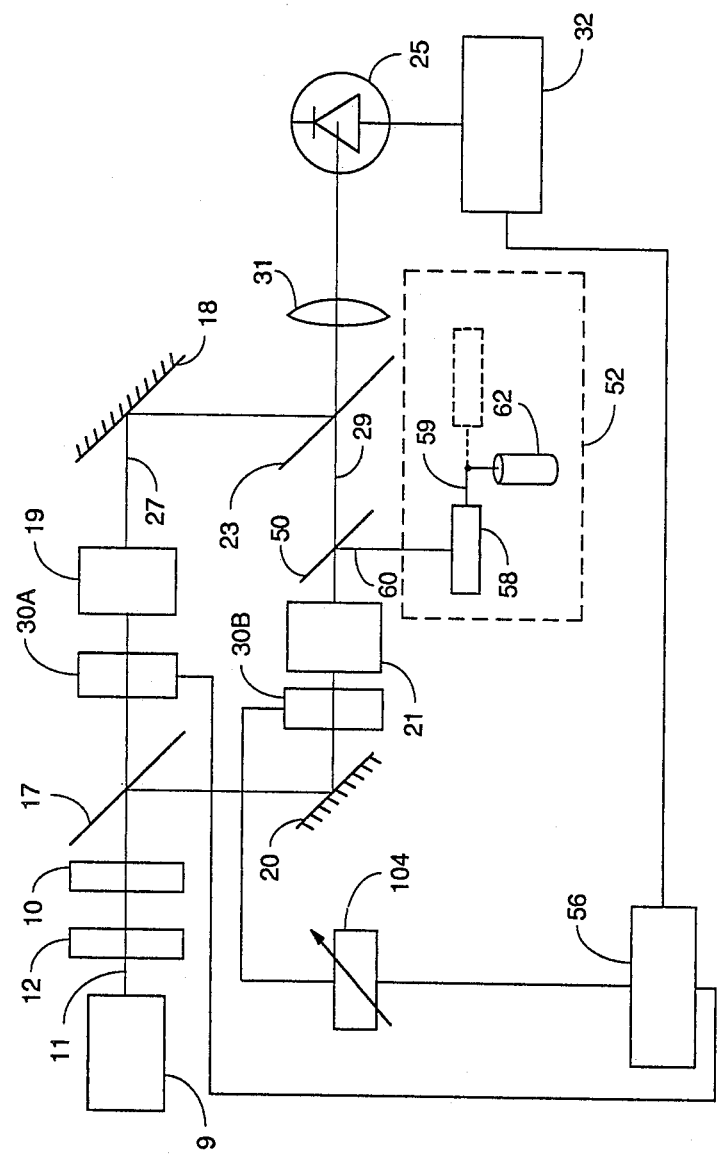
FIG. 4B shows an alternative embodiment of the apparatus of FIG. 4A which has very low noise characteristics.

A variation of the embodiment illustrated in FIG. 4A which has even better noise characteristics is shown in FIG. 4B. In this embodiment, two acousto-optical modulators 30A and 30B are used, one in each arm, to shift the beam frequency in each arm by RF frequencies $f_1$ and $f_2$, respectively, just as was done for the embodiment of FIG. 2C. RF power for the modulators is provided by power module 56, as hereinbefore described with reference to FIG. 2D.

The above approaches to providing a well-calibrated optical beam are especially useful for achieving very low optical power levels, power levels which have heretofore been generally quite difficult to attain with any degree of accuracy in the calibration.

Measurements of BRDF

Another important application for the heterodyne receiver according to the invention is in measuring the bidirectional reflectance distribution function (BRDF) or the bidirectional transmittance distribution function (BTDF) of a surface. Generally, the BRDF of a surface is defined to be the ratio of the reflected radiance to the incident irradiance. Hence, the BRDF of a surface is dependent on four angular coordinates, i.e. the two angles used for describing the incidence direction and the two angles used for describing the direction of scattering (reflection). In general then $$R'(\theta_i, \phi_i, \theta_r, \phi_r) = \frac{dN_r}{dH_i}$$

where $R'$ is the BRDF (per steradian) and $\theta_i$ and $\phi_i$ describe the angle of incidence and the azimuth of the incident beam (using standard definitions for angles in a Euclidean X-Y-Z coordinate system), and $\theta_r$ and $\phi_r$ describe the equivalent angles for the scattered beam direction. $dN_r$ is the reflected radiance in Watts/(m²sr) and $dH_i$ is the incident irradiance in Watts/m². For a narrow, collimated, incident beam, and a detector with a narrow field of view, the BRDF is generally written as:

$$R' = \frac{P_r}{P_i \Omega \cos\theta_r}$$

Where $P_r$ is the scattered power measured by the detector, $P_i$ is the incident power, $\Omega$ is the solid angle subtended by the detector aperture, and $\cos\theta_r$ accounts for the change in the projected illuminated area with reflection angle. (See "The Theory and measurement of bidirectional reflectance distribution function (BRDF) and bidirectional transmittance distribution function (BTDF)", by P. O. Bartell et al, SPIE Vol. 257, Radiation Scattering in Optical Systems (1980), pp. 154-160; and "Directional Reflectance and Emissivity of an Opaque Surface", by F. E. Nicodemus, APPLIED OPTICS, July 1965, Vol. 4, No. 7, pp. 767-773; and "Role of scattering distribution functions in spacecraft contamination control practices", by P. A. Carossa et al, APPLIED OPTICS, Vol. 25, No. 7, April 1986, pp. 1230-1234; each of which is incorporated herein by reference.)

For a heterodyne detector system, the solid angle of the detector is diffraction limited, where the diffraction limit is determined by the size of the local oscillator beam. Hence, $$\Omega = \frac{\lambda^2}{\pi w_0^2}$$

where $w_0$ is the $1/e^2$ radius of the irradiated spot on the surface. Therefore the heterodyne BRDF is $$R' = \frac{P_r}{H_i \lambda^2 \cos\theta_r}$$

Figure 5A:
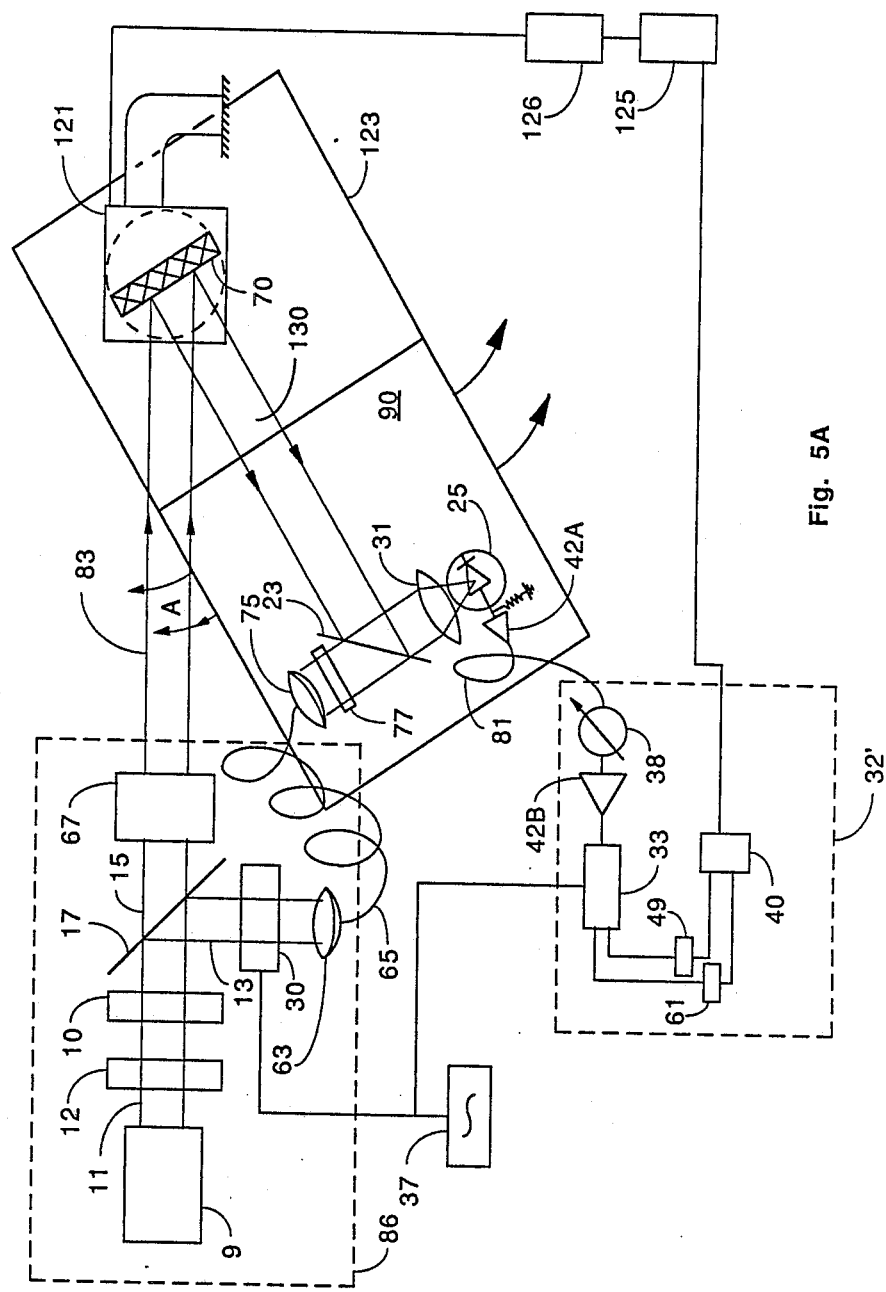
FIG. 5A shows an apparatus according to the invention for measuring the BRDF of surfaces.
Figure 5B:
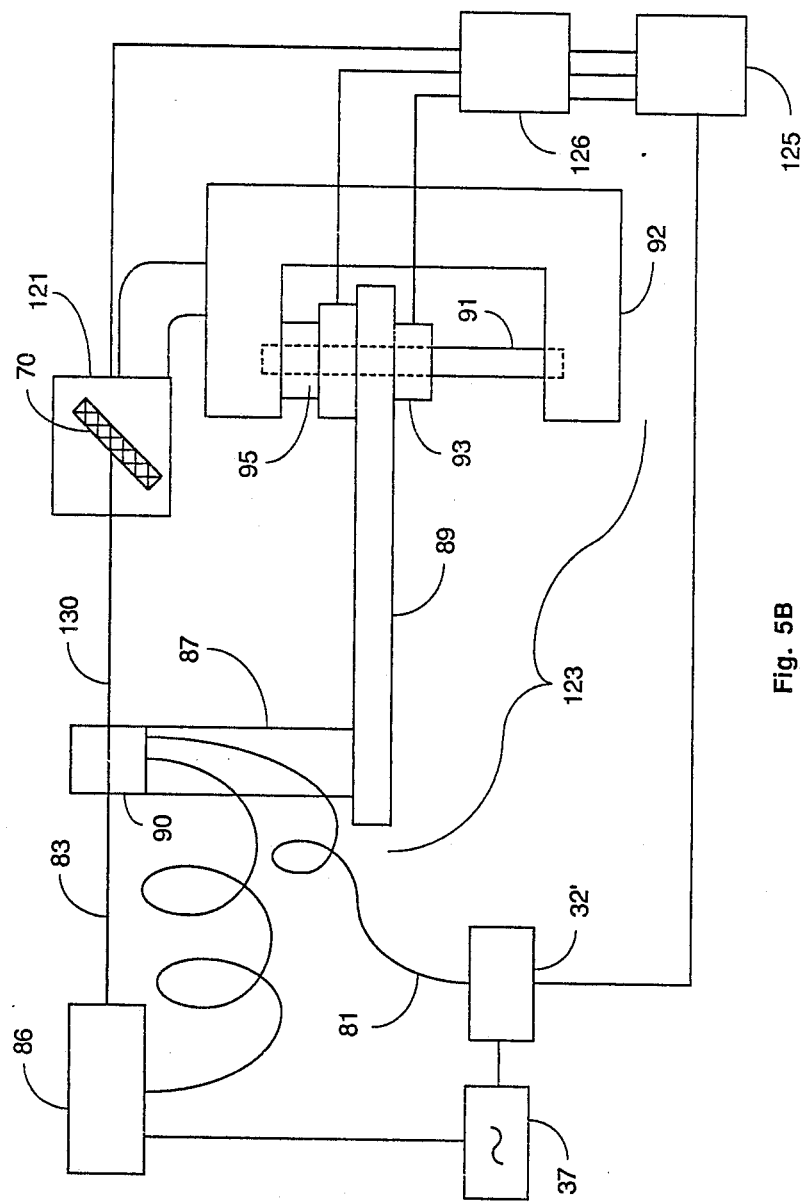
FIG. 5B shows a side view of the apparatus of FIG. 5A.

An apparatus according to the invention for measuring the heterodyne BRDF is shown schematically in FIGS. 5A and 5B. In this embodiment, the laser 9 is isolated by optical isolator 12, and the incoming beam is stabilized by intensity stabilizer 10 as before. The beam is then split by beam splitter 17 into beams 13 and 15. Beam 13 is frequency shifted by acousto-optic modulator 30, and the frequency shifted beam impinges on a mode matching lens 63 used for matching the beam characteristics to a single mode, polarization preserving, optical fiber 65 which is used for conducting the light in one arm of the interferometer. In the other arm of the interferometer, beam 15 is adjusted in size by collimating telescope 67, so that the desired area of a surface 70 is illuminated, surface 70 being the surface for which the BRDF is to be determined. In the most general case, surface 70 is mounted on a goniometer 121, i.e. a two axis gimballed mount having accurate angle readout. Such two axis gimballed mounts are well known in the industry and include precision drives for rotating the surface about orthogonal axes in the plane of the surface in order to achieve any desired orientation of the surface to be tested. A laser heterodyne detector 90 of the interferometer system is mounted on a swing arm assembly 123 typically mounted above or below the gimballed mount 121, for example as illustrated in the side view shown in FIG. 5B which will be discussed subsequently.

Heterodyne detector 90 is similar to the detector portion in previous embodiments and includes another mode matching lens 75, and collimating telescope 77 for collimating and matching the beam sizes in the two arms. Also included is beam splitter 23 which is used to combine the beams from the two arms, and lens 31 focuses the resulting beam onto fast photodetector 25 as before. Both lens 31 and photodetector 25 are included in detector portion 90.

The output terminal of the photodiode is connected to preamplifier 42A as before and the output of 42 A is connected by flexible cable 81 to element 32', which is simply the balance of heterodyne RF power detector 32 that has been already been described earlier. This flexible connection permits rotation of the swing arm 123 through a succession of angles A, in order to determine the BRDF.

An example of the physical layout of the swing arm assembly 123 is shown in more detail in FIG. 5B. Beam 83 emanating from collimating telescope 67 is shown schematically as arising from element 86 which is shown in FIG. 5A as a dotted box. Beam 83 impinges on the scattering surface 70 and a portion 130 of the beam is scattered in the direction of the detector portion 90. Detector portion 90 is mounted on a vertical extension 87 to bring the detector portion 90 into the plane of the laser interferometer. The vertical extension 87 is attached to an arm 89 constrained to swing in a horizontal plane about a shaft 91 which is mounted in line with the horizontal axis of rotation of the goniometer 121. Shaft 91 is mounted in a frame member 92, and attached to the shaft is a shaft encoder 93 for accurately determining the angle A through which the arm 89 has been swung. A motor 95 is used to turn the shaft 91 and arm 89. In the preferred mode, the goniometer, the motor, and the encoder are connected to a computer 125 via a control interface 126, in order to automatically step the arm 89 through a set of predetermined angles A, and to move the goniometer through the desired orientations of the surface 70. Input from the RF power detector 32 is used by computer 125 to calculate the BRDF for the various orientations of the surface and for the various angles A that are chosen.

The angular resolution of the heterodyne detector 90 is given by $\delta\theta \approx \lambda/2D$. For a Nd YAG laser, at $\lambda = 1.06$ micrometers, and for a 1 cm diameter local oscillator beam, $\delta\theta \approx 3 \times 10^{-5}$. Hence, to measure a single 90 degree arc would approximately $3 \times 10^4$ measurements.

Generally the time required for each measurement is dependent on the sensitivity of the detector 90, i.e. its signal to noise ratio. In those situation where the shot noise is the limiting element, the sensitivity is given by $$R'_{min} = \frac{P_{SN}}{H_i \lambda^2 \cos\Theta}$$

where $P_{SN}$ is the shot noise limit in Watts. For a 10 mW laser beam illuminating the sample, the sensitivity is $R'_{min}/\delta f = 1.3 \times 10^{-9}/(sr\ Hz)$, where $\delta f$ is the measurement bandwidth. Typically, a sensitivity of $10^{-7}/sr$ is sufficient for most BRDF measurements. Hence, a measurement bandwidth of $10^2$ Hz is sufficient. A measurement over a 90 degree arc in that case would require only about 60 seconds.

Those skilled in the art will appreciate the importance of this particular detection approach, in that measurements can be made remotely. For example, it can be arranged such that all electrically active components are located outside of an enclosed chamber and the optical beams can be fed through, either through fibers or windows, or some combination thereof, so that scattering measurements can be made for surfaces located in hazardous, or high vacuum or ultraclean environments. It also allows measurements to be made on surfaces as they are being produced.

Those skilled in the art will realize that there are many equivalent embodiments of the above detection system which have not been discussed in detail. For example, although most embodiments described have the acousto-optic modulator located in the test arm, the required frequency shift could be introduced into either arm of the interferometer, and at any location in either arm as long as it is introduced before the coherent mixing element (beam splitter 23). Similarly, there are many equivalent ways of obtaining two coherent optical beams which are shifted in frequency relative to each other in addition to the approach described using an acousto-optic modulator. For example, one could use two frequency-locked lasers, or one could use a laser operating in two frequencies in conjunction with a means for separating the output into two beams. Also, it should be apparent that the approach illustrated in FIGS. 2C, 2D, and 4B, utilizing two acousto-optic modulators to produce the desired frequency shifts, and thereby reducing electromagnetic interference, could also be used in all of the other embodiments. Those skilled in the art will also understand that in some situations, the power stabilizer 10 may not be required, and that some lasers may not require an isolator 12. However good practice is generally toward using an isolator to stabilize the output of the laser and to reduce spurious effects due to scattered light. Also, it should be apparent to those skilled in the art, that one could replace the single photodetector 25 with a balanced heterodyne photodetector pair to increase the signal to noise ratio. (H. P. Yuen and V. W. S. Chan, Opt. Lett. 8. 177(1983). This is particularly important when the system is limited not by shot noise, but by laser technical noise. Also, although only measurement of BRDF has been described in detail, it will be apparent to those skilled in the art that the above techniques can be applied as well to measurements of the bidirectional transmittance distribution function, by simply moving the detector portion 90 behind the surface 70 in order to measure the RF power corresponding to the transmission of the beam at various angles.

What is claimed is:

1. An apparatus for measuring optical power comprising:
    means for producing two optical beams such that at some point and thereafter along an optical path of the beams, a well defined frequency difference exists between the two beams, one of the two beams having a known or constant optical power, said beam hereinafter called the reference beam, and the other of the two beams being the beam whose power is to be measured, said measured beam hereinafter called the test beam;
    combining means for coherently combining the two optical beams;
    optical detection means for receiving the combined two optical beams, and in response thereto for providing an electrical signal that is modulated at the difference frequency of the optical fields of the two optical beams, the electrical signal being functionally related to the heterodyne product of the two fields;
    electrical power detector means for measuring the electrical power of said electrical signal.

2. An apparatus as in claim 1 wherein the electrical power detector means comprises a heterodyne detection system referenced to the difference frequency of the two beams.

3. An apparatus as in claim 1 further comprising insertion means for inserting and removing a filter from the path of the test beam, so that the resulting change in the heterodyne product of the two optical powers with the filter in the path of the test beam relative to not having the filter in the test path can be measured by measuring the change in electrical power.

4. An apparatus as in claim 3 wherein the electrical power detector means comprises a heterodyne detection system referenced to the difference frequency of the two beams.

5. An apparatus as in claim 1 further comprising:
    means for focussing the test beam onto a photographic plate so as to attenuate the test beam in a manner related to the local optical density of the photographic plate where the beam is focussed; and
    means for recollimating and outputting the test beam to the combining means after transmission through the photographic plate.

6. An apparatus as in claim 5 further comprising translation means for moving the photographic plate so that the test beam is focussed onto different portions of the photographic plate at different times.

7. An apparatus as in claim 6 wherein the electrical power detector means comprises a heterodyne detection system referenced to the difference frequency of the two beams.

8. An apparatus as in claim 1 further comprising:
goniometer means for holding a surface in the path of the test beam in a desired orientation relative to the incidence direction of the test beam;
moving means for moving the optical detector means so as to receive light from one or a plurality of known second directions that is scattered or transmitted from the surface as a result of the incidence of the test beam on the surface; and
calculation means for calculating the ratio of the radiance in the one or plurality of known second directions to the incident irradiance of the test beam.

9. An apparatus as in claim 8 wherein said moving means comprises a platform on which the optical detector means is mounted, the platform being rotatable about said surface.

10. An apparatus as in claim 9 wherein said reference beam is transmitted to said optical detector mean by means of an optical fiber.

11. An apparatus as in claim 10 wherein the electrical power detector means comprises a heterodyne detection system referenced to the difference frequency of the two beams.

12. An apparatus as in claim 1 further comprising:
attenuator means for varying the optical power in the test beam;
beam splitter means located in the test path for removing a constant fraction of the test beam to provide an output beam;
optical power measuring means for measuring the power in the output beam; and
insertion means for inserting and removing the optical power measurement means from the output beam, so that an attenuated test beam can be provided.

13. An apparatus as in claim 12 wherein the electrical power detector means comprises a heterodyne detection system referenced to the difference frequency of the two beams.

* * * * *